US00PP31601P2

(12) United States Plant Patent
Hansen

(10) Patent No.: US PP31,601 P2
(45) Date of Patent: Mar. 24, 2020

(54) **X *MANGAVE* PLANT NAMED 'SHADOW WALTZ'**

(50) Latin Name: **x *Mangave* hybrid; *Manfreda* times *Agave***
Varietal Denomination: Shadow Waltz

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/501,795

(22) Filed: Jun. 7, 2019

(51) Int. Cl.
*A01H 5/00* (2018.01)
*A01H 6/12* (2018.01)

(52) U.S. Cl.
USPC ..... Plt./373
CPC ..... *A01H 6/12* (2018.05)

(58) Field of Classification Search
USPC ..... Plt./373
CPC ..... A01H 5/00
See application file for complete search history.

*Primary Examiner* — Kent L Bell

(57) ABSTRACT

A new and unique x *Mangave* plant named 'Shadow Waltz' characterized by a medium mound of broad, fleshy, mostly flat foliage with small flexible cream-colored marginal teeth and lacking sharp terminal spine. Foliage is upright to outwardly toward stem with a tendency to arch in maturity. The numerous flowers are upright to slightly outwardly, a mixture of yellowish-chartreuse becoming blushed or speckled with red in maturity, formed on stiff, branched stalks. The new plant is suitable for the garden or as a potted plant in the garden or home.

2 Drawing Sheets

Botanical classification: x *Mangave* hybrid; *Manfreda* times *Agave*.

Variety denomination: 'Shadow Waltz'.

STATEMENT REGARDING PRIOR DISCLOSURES UNDER 37 CFR 1.77(B)(6)

The first non-enabling disclosure of the claimed plant, in the form of a photograph and brief description on a website operated by Walters Gardens, Inc. on Feb. 14, 2019. The claimed plant was first sold on Jul. 23, 2018 privately by Walters Gardens, Inc. to Plant Delights Nursery. Walters Gardens, Inc. obtained the new plant and all information relating thereto, from the inventor. No plants of x *Mangave* 'Shadow Waltz' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to the new and distinct x *Mangave* hybrid plant, x *Mangave* 'Shadow Waltz' that was hybridized by the inventor at a wholesale perennial nursery in Zeeland, Mich., USA as a cross between an unnamed proprietary hybrid referenced as H10-08 as the female or seed parent times a proprietary selection of *Agave nizandensis* (not patented) as the male or pollen parent. The cross was performed on Apr. 10, 2014 and seeds were harvested and sown in the summer of 2014. Through trials at the same nursery the plant was assigned the breeder code 14-34-22. The new plant has been successfully asexually propagated first by removal of basal offsets at the same nursery in Zeeland, Mich. and later by sterile shoot-tip tissue culture. The asexual propagation has been found to produce stable and identical plants that maintain all the unique characteristics of the original plant in multiple generations.

BRIEF SUMMARY OF THE INVENTION x *Mangave* 'Shadow Waltz' differs from its parents as well as all other *Manfreda, Agave* and x *Mangave* known to the applicant. The female parent has foliage that is wider, has larger marginal teeth and has significant mahogany mottling or spotting on both upper and lower surfaces. The male parent is more horizontal in habit, slower growing, with narrower foliage, and fewer flowers that have narrower tepals of slightly deeper yellow on scapes without branching. The nearest comparison plants are 'Racing Stripes' U.S. Plant Pat. No. 31,251 and 'Painted Desert' copending U.S. Plant patent application Ser. No. 16/501,796. 'Racing Stripes' has wider leaves with larger, firmer, cinnamon-colored, marginal teeth and significant marginal spines with more upright habit. 'Painted Desert' has foliage that develops a heavy reddish-purple spotting in high ultraviolet light exposure.

The new plant, 'Shadow Waltz', is unique from all of the above cultivars and all *Agave*, x *Mangave* and *Manfreda* known to the inventor by the following combined traits:

1. Arching mound of stiff, long, narrow foliage;
2. Leaves have small, flexible, cream-colored marginal teeth;
3. Leaf margins lacking sharp firm apical spine;
4. Leaves with broad dark green margin and light green to chartreuse center;
5. Numerous upright to slightly outwardly flowers on cylindrical, upright, branched stalk;
6. Flowers are mixtures of yellowish-chartreuse lightly speckled or blushed with red in maturity;

7. Moderate growth rate;
8. Foliage is upright to slightly outwardly toward stem.

BRIEF DESCRIPTION OF THE DRAWING

The photograph of x *Mangave* 'Shadow Waltz' demonstrates the overall appearance of the new plant including the unique traits as a three-year-old plant grown in a container in Zeeland, Mich. The colors are as accurate as reasonably possible with color reproductions. Ambient light spectrum, temperature, source and direction may cause the appearance of minor variation in color.

DETAILED BOTANICAL DESCRIPTION

Figure 1:
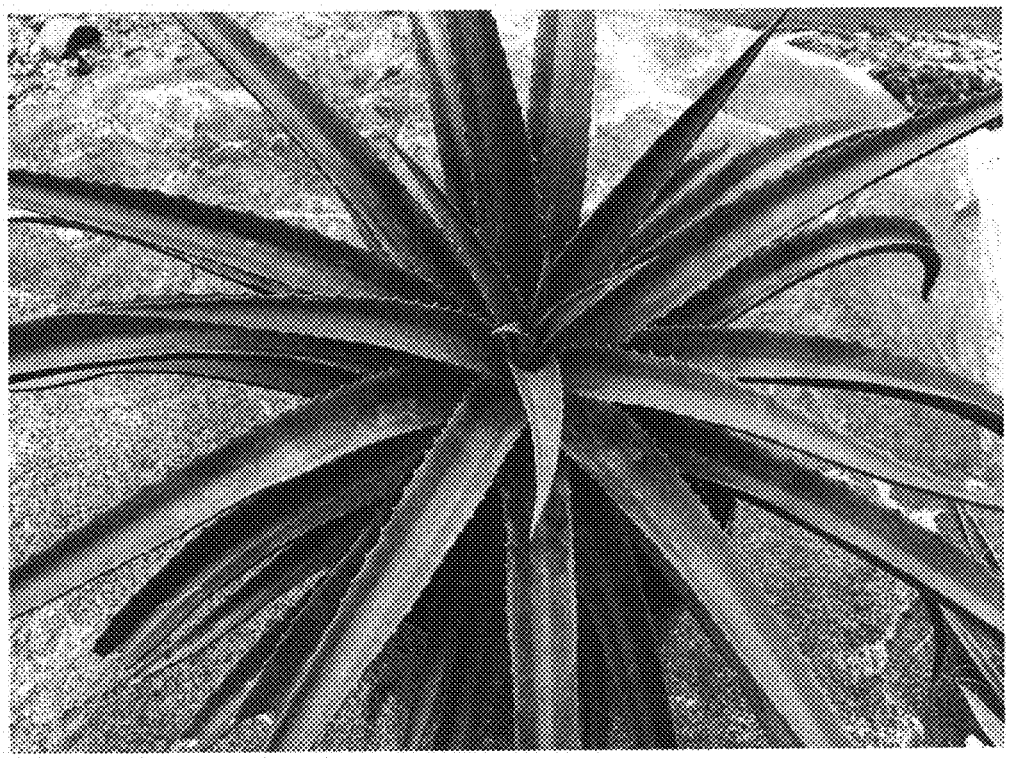
FIG. 1 shows a top view of a containerized plant that was grown in a full-sun trial garden.
Figure 2:
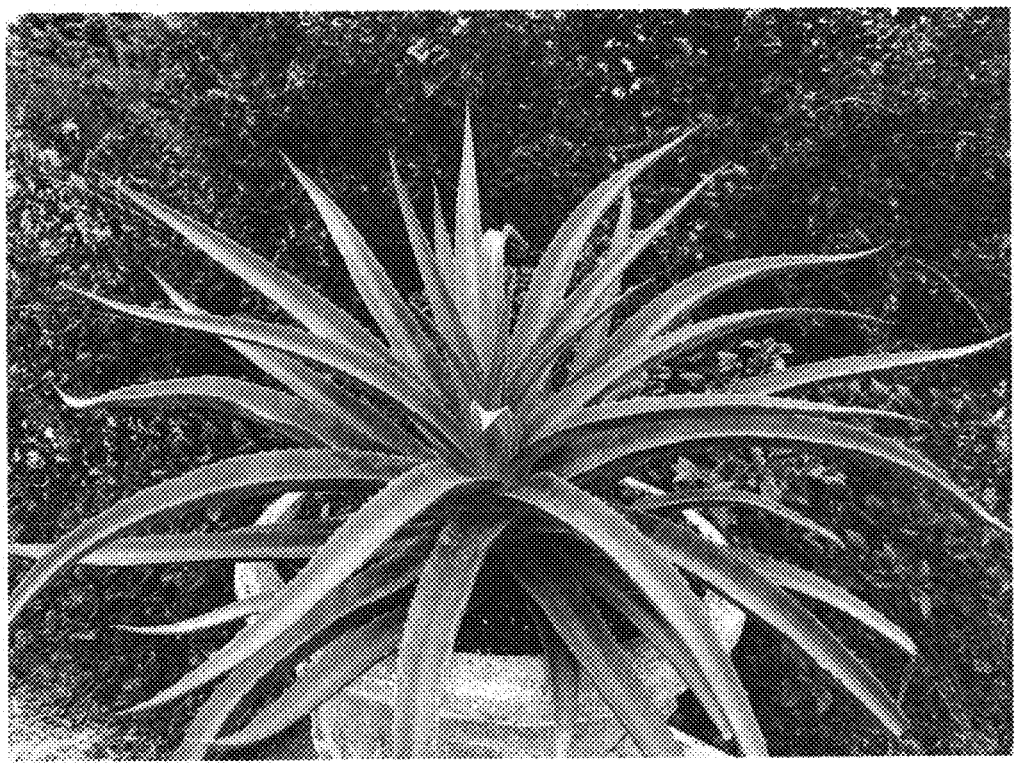
FIG. 2 shows a side view of the plant that was grown in a full-sun trial garden.
Figure 3:
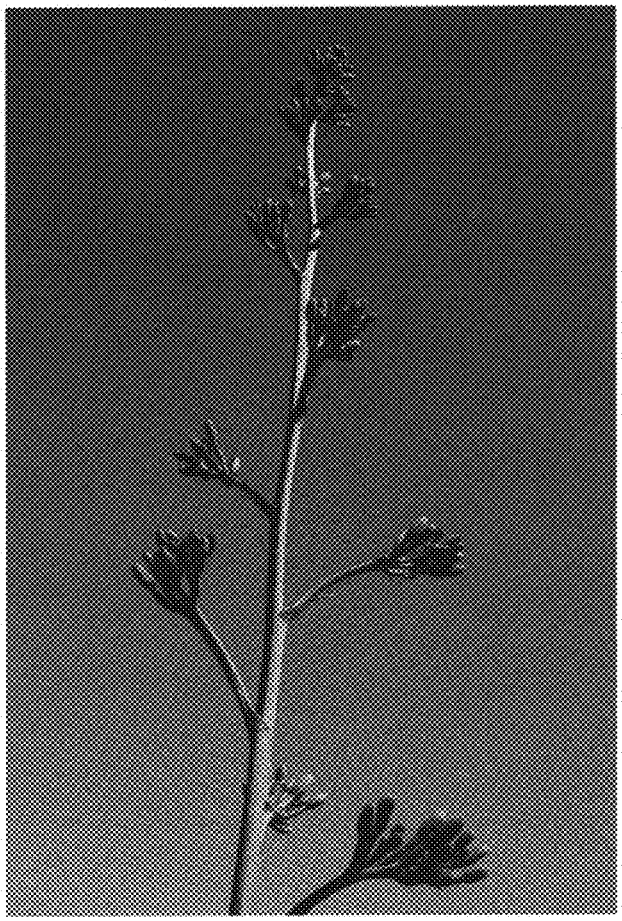
FIG. 3 shows the upper portion of the flower stalk with branching.
Figure 4:
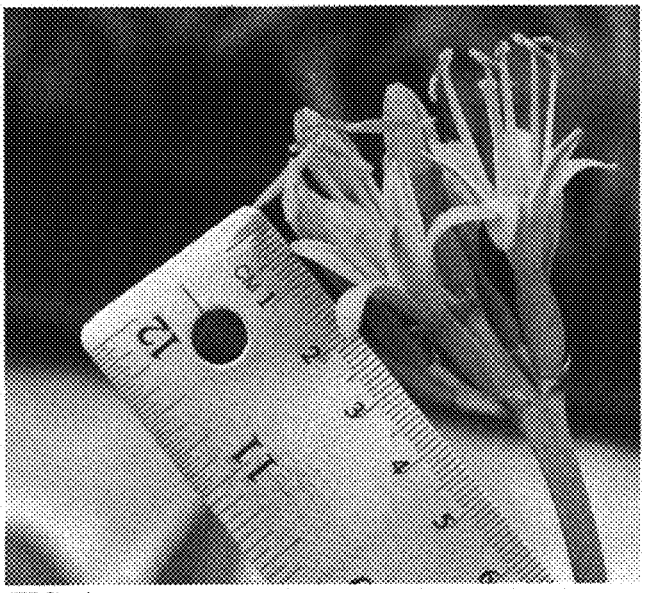
FIG. 4 shows a close-up of the flowers and buds at various stages.

The following descriptions and color references are based on the 2015 edition of The Royal Horticultural Society Colour Chart except where common dictionary terms are used. The new plant, x *Mangave* 'Shadow Waltz', has not been observed under all possible environments. The phenotype may vary slightly with different environmental conditions, such as temperature, light, fertility, moisture and maturity levels, but without any change in the genotype. The following observations and size descriptions are of a four-year-old plant in a commercial wholesale greenhouse and in a full-sun trial garden in Zeeland, Mich. with supplemental water and fertilizer as needed.

Parentage: An unnamed proprietary hybrid known as H10-08 as female or seed patent and an unnamed selection of *Agave nizandensis* as the male or pollen parent; H10-08 is a cross between x *Mangave* 'Bloodspot' (not patented) and *Agave parryi integrifolia* an unnamed selection (not patented);

Propagation: By sterile shoot-tip tissue culture;

Time to initiate roots from tissue culture: About 21 days;

Growth rate: Moderate to slow;

Crop time: About 16 to 20 weeks to finish in a 3.8 liter container from a 35 mm tissue culture growing at about 21° C.;

Rooting habit: Fleshy, lightly branching, with roots up to 30 cm long;

Root color: Nearest RHS 158C;

Plant shape and habit: Succulent herbaceous perennial with basal rosettes of about 56 leaves radially emerging outwardly from central stem prior to flowering, producing a radially-symmetrical, rounded mound;

Plant size: Foliage height about 26.0 cm tall from soil line to the top of the leaves and about 70.0 cm wide at the widest point about middle of the plant; flowering to 162.0 cm;

Foliage description: Lanceolate; simple; sessile; bi-laterally symmetrical; sarcous; apex narrowly acute without terminal spine; base truncate; mostly flat with flat margins; margins finely dentate; glabrous abaxial and adaxial; abaxial and adaxial dull becoming slightly lustrous adaxial and abaxial;

Marginal teeth: With small flexible teeth that become firm with maturity; about 2.0 mm long and 2.0 mm wide at base; average about 7.0 mm apart on mature leaves;

Terminal spine: Absent;

Leaf size: To about 34.5 cm long, about 4.0 cm wide at base; center base about 7.0 mm thick at basal midrib; average about 32.0 cm long, 3.8 cm wide and 8.0 mm thick in longitudinal center;

Foliage fragrance: None observed;

Leaf number: About 56 per plant;

Leaf blade color:

*Adaxial* (*mature*).—In lower ultraviolet light exposure margin nearest RHS 137B and center nearest RHS 146C, in high ultraviolet exposure margin nearest RHS 139A and center RHS 147B.

*Abaxial* (*mature*).—In lower ultraviolet light exposure margin nearest RHS 137C and center nearest RHS 146C; in high ultraviolet light exposure margin nearest RHS 137A and center between RHS 146A and RHS 146B.

*Adaxial* (*young*).—Margins nearest RHS 137 C and between RHS 145A and RHS 146D in center.

*Abaxial* (*young*).—Margins nearest RHS 137 C and between RHS 145A and RHS 146D in center.

*Marginal teeth*.—Nearest RHS 155D when young, becoming nearest RHS 155A at apex and nearest RHS 139A at base.

Petiole: Leaves sessile;

Veins: Parallel; not distinct abaxial or adaxial;

Inflorescence description: Cylindrical; stiff, ridged, upright, branched panicle; glaucous; glabrous; to about 162.0 cm tall and 18.0 mm diameter at base; about 28 branches extending at about a 45 degree angle to about 15.0 cm long and 4.0 mm diameter at base; flowering portion about 122.0 cm long and 26.0 cm across;

Cauline leaves: About 15 per scape before branches; lanceolate; simple; fleshy; glaucous; glabrous; margins finely dentate with flexible teeth; apex narrowly acute without mucro; base truncate, sessile, clasping; proximally about 18.5 cm long and about 2.0 cm wide at base, decreasing distally;

Cauline leaf color: Young adaxial nearest RHS 137C in margins and nearest RHS 145A in center, abaxial nearest RHS 146B margins and nearest RHS 146D in center with fine but dense speckling of nearest RHS 183A; older and lower cauline leaf color same as basal leaves;

Buds one day prior to opening: Elongated globose; about 28.0 mm long and about 9.0 mm across at mid-tepal, ovary base about 4.0 mm diameter;

Bud color: Nearest RHS 146C;

Flowers: Perfect, actinomorphic; about 4.8 cm long to end of anthers and opening to about 2.8 cm across at outside of anthers and 5.0 mm diameter at ovary; lasting about 3 to 4 days per flower; flowering period about three weeks in late spring or when mature in Michigan greenhouse; producing abundant nectar; approximately 400 flowers per scape; attitude mostly upright to slightly outwardly; moderately densely arranged on branches;

Flower fragrance: Not detected;

Tepals: Six in two sets of three; glaucous abaxial and slightly lustrous adaxial; glabrous both adaxial and abaxial; acute apex and fused base; outer set about 25.0 mm long to top of ovary, fused in about basal 12.0 mm and about 6.0 mm wide at base; inner set about 25.0 mm long to top of ovary and 7.0 mm wide at fusion; inner set creased along margin where overlapped with outer set while in bud; outer tepals recurved 180 degrees;

Tepal color: Variable; young adaxial outer tepal nearest RHS 145A; young abaxial outer tepal base nearest RHS NN137B, middle nearest RHS 147B maculate with nearest RHS 187A; young adaxial inner tepal margin nearest RHS 150D, center nearest RHS 145A; young abaxial inner tepal base nearest RHS NN137B, middle margin nearest RHS 145C, center nearest RHS 147B lightly maculate with nearest RHS 187A; mature abaxial outer tepal base nearest RHS 145A blushed with nearest RHS 187A; mature abaxial inner tepal margin nearest RHS 150D with light blush of nearest RHS 187A and center nearest RHS 145A with blush nearest RHS 187A; mature adaxial outer tepal nearest RHS 145A with blush nearest RHS 187A; mature adaxial inner tepal margin nearest RHS 150D with blush nearest RHS 187A and center nearest RHS 145A with blush nearest RHS 187A;

Androecium: Six;

*Filaments*.—Six; adnate to inner tepals in basal 8.0 mm; cylindrical distally, slightly applanate toward base; stiff and straight; about 26.0 mm long and 1.5 mm diameter at base; color distally nearest RHS 154D and proximally nearest RHS 150C lightly blushed with nearest RHS 176C.

*Anther*.—Dorsifixed; longitudinal; about 16.0 mm long and 2.0 mm diameter before opening; after dehiscence remaining straight; color nearest RHS N144A.

*Pollen*.—Abundant, clumpy and rarely fluffy; color nearest RHS 2A.

Gynoecium: Single; 46.0 mm long;

*Style*.—26.0 mm long and 2.0 mm diameter at base; color nearest RHS 2C.

*Stigma*.—Turbinate, apex tri-lobed; about 2.0 mm tall and 3.5 mm across top; color nearest RHS 196D when young, developing to nearest RHS 160D with base blushed nearest RHS 187A.

*Ovary*.—Inferior; to 18.0 mm long and 6.0 mm wide; color nearest RHS 137B.

Peduncle: Cylindrical; glaucous; glabrous; to 162.0 cm long and 18.0 mm diameter at base; flowering in upper 122.0 cm to about 25.0 cm wide; with about 27 branches, cauline leaves and bracts subtending branches;

Branches: With 4 to 32 flowers per branch; held upright to arching distally, beginning about a 45 degree angle above horizontal, and arching to about 25 degrees above horizontal; slightly flattened toward base, to about 15.0 cm long, 5.0 mm wide and about 3.0 mm thick;

Peduncle color: Nearest RHS 138A in low ultraviolet light and in high ultraviolet light developing to a blend nearest RHS 147B and RHS 187A;

Cauline leaves: About 13 per peduncle; distal leaves adpressed to peduncle; lanceolate with narrowly acute apex, truncate clasping base and small, flexible, marginal teeth; to about 17.0 mm long and 18.0 mm wide at base and 2.0 mm thick, decreasing distally;

Cauline leaf color: In low ultraviolet light abaxial and adaxial center nearest RHS 145A and abaxial and adaxial margins nearest RHS 138A; in high ultraviolet light developing reddish blush to nearest blend between RHS 183C and RHS 53B on abaxial side and blend between RHS 147B and RHS 183C on adaxial side; teeth nearest RHS 158D;

Bracts: Below peduncle branches; lanceolate with narrowly acute apex and clasping truncate base; to about 40.0 mm long and 20.0 mm wide at base;

Bract color: Abaxial center nearest RHS 178B and abaxial margin nearest RHS 177B; adaxial center nearest blend between RHS 147D and RHS 146D and margin nearest RHS 177B;

Pedicel: Cylindrical; glabrous; glaucous; average about 3.0 mm long and 3.0 mm diameter;

Pedicel color: Between RHS 146C to RHS 146D;

Fruit: Dehiscent, tri-valved, loculicidal capsule; apex broadly acute with base slightly tapered; about 25.0 mm long and 10.0 mm across;

Fruit color: When immature nearest RHS 138A lightly tinted with nearest RHS N187A; pods have not yet dehisced;

Seed: Have not yet been harvested;

Disease resistance: X *Mangave* 'Shadow Waltz' has not been observed to be resistant to diseases beyond that which is normal for x *Mangave, Agave* or *Manfreda*. The new plant is xeromorphic and survives well with minimal water once established. The new plant is estimated to be hardy at least from USDA zone 9. Full extent of winter hardiness has not been tested.

It is claimed:

1. A new and distinct cultivar of ornamental x *Mangave* plant named 'Shadow Waltz' as herein described and illustrated.

* * * * *